United States Patent [19]

Kawamura et al.

[11] Patent Number: 4,469,864
[45] Date of Patent: * Sep. 4, 1984

[54] THIOPYRYLIUM COMPOUNDS AND PHOTOCONDUCTIVE COMPOSITIONS CONTAINING SAID COMPOUNDS

[75] Inventors: Kouichi Kawamura; Hideo Sato; Harumi Katsuyama, all of Saitama, Japan

[73] Assignee: Fuji Photo Film Co., Ltd., Kanagawa, Japan

[*] Notice: The portion of the term of this patent subsequent to Feb. 16, 1999 has been disclaimed.

[21] Appl. No.: 425,773

[22] Filed: Sep. 28, 1982

Related U.S. Application Data

[62] Division of Ser. No. 294,644, Aug. 20, 1981, Pat. No. 4,389,474.

[30] Foreign Application Priority Data

Aug. 20, 1980 [JP] Japan .............................. 55-114259

[51] Int. Cl.$^3$ ........................................... C07D 333/02
[52] U.S. Cl. ..................................................... 549/13
[58] Field of Search ........................... 549/13; 542/454

[56] References Cited

U.S. PATENT DOCUMENTS

| | | | |
|---|---|---|---|
| 3,501,307 | 3/1970 | Illingsworth | 96/101 |
| 4,148,900 | 4/1979 | Doria et al. | 542/454 X |
| 4,315,983 | 2/1982 | Kawamura et al. | 549/13 X |
| 4,343,948 | 8/1982 | Kawamura et al. | 549/13 |

FOREIGN PATENT DOCUMENTS 1161780 8/1969 United Kingdom .

*Primary Examiner*—Richard Raymond
*Attorney, Agent, or Firm*—Sughrue, Mion, Zinn, Macpeak and Seas

[57] ABSTRACT

A thiopyrylium compound having t-butyl groups at the 2- and 6-positions of the thiopyrylium nucleus, having a main absorption near the red region, i.e., 600 to 700 nm but substantially no side absorption near 400 nm, and useful as a sensitizer for a photoconductive composition.

1 Claim, 5 Drawing Figures

THIOPYRYLIUM COMPOUNDS AND PHOTOCONDUCTIVE COMPOSITIONS CONTAINING SAID COMPOUNDS

This is a division of application Ser. No. 294,644, filed Aug. 20, 1981, now U.S. Pat. No. 4,389,474.

FIELD OF THE INVENTION

This invention relates to thiopyrylium compounds and a process of producing the pyrylium compounds. The invention further relates to photoconductive compositions containing the thiopyrylium compounds.

BACKGROUND OF THE INVENTION

It is known that thiopyrylium dyes or pyrylium dyes can be used for various purposes. For example, they can be used for direct positive photographic silver halide emulsions as electron acceptors as described in Japanese Patent Application (OPI) No. 40,900/71 (the term "OPI" as used herein refers to a "published unexamined Japanese patent application") and also they are useful as spectral sensitizers for photoconductors, in particular as spectral sensitizers for organic photoconductors as described in U.S. Pat. Nos. 3,141,700, 3,250,615, and 3,938,994, and in *Research Disclosure*, 19321, page 5 (November, 1977).

Photoconductors sensitized with thiopyrylium dyes or pyrylium dyes can be used for various purposes as disclosed in the above-illustrated patents but they are particularly important for xerography and Electrofax-system electrophotography.

However, conventionally known thiopyrylium dyes are unsatisfactory for obtaining a photoconductive composition having a sufficiently high sensitivity to light in the red region (600–700 nm) and hence it has further been desired to improve the sensitivity of photoconductive compositions.

Since conventionally known thiopyrylium compounds have a substituent which is conjugatable to the thiopyrylium nucleus or a condensed ring of a conjugatable nucleus, such compounds have a side absorption near the blue region, i.e., a wavelength of 400 nm and a photoconductive composition prepared using such a thiopyrylium compound frequently results in an undesirable yellow-mixed colored photosensitive composition, and the composition has a disadvantage that the yellow-mixed coloration further increases when the composition is exposed over a long time, because dyes included in the composition decompose by the exposure over a long time to decrease a red-region absorption and to increase, on the contrary, blue-region absorption.

SUMMARY OF THE INVENTION

As the result of various investigations to overcome these difficulties, thiopyrylium compounds, which have excellent sensitizing capability in comparison with known red sensitive sensitizers as a sensitizer for photoconductors, which do not have side absorption near the blue wavelength region, and which impart not so much yellow-mixed coloration on a photo-discoloration, have been discovered.

By using the thiopyrylium compounds of this invention, preferred blue electrophotographic photosensitive materials with very high sensitivity to light in the red region and without yellow color mixing are obtained.

An object of this invention is to provide thiopyrylium compounds having excellent characteristics.

Another object of this invention is to provide a photoconductive composition comprising a photoconductive material containing a thiopyrylium compound as a sensitizer.

Accordingly, this invention provides a thiopyrylium compound represented by general formula (I)

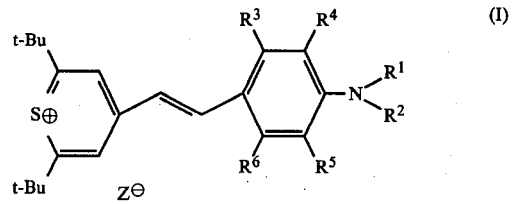

wherein t-Bu represents a tert-butyl group; $R^1$ and $R^2$, which may be the same or different, each represents a hydrogen atom, an alkyl group having 1 to 5 carbon atoms, a substituted alkyl group, an unsubstituted aryl group or a substituted aryl group; with the proviso that $R^1$ and $R^2$ are not simultaneously an alkyl group; $R^3$, $R^4$, $R^5$ and $R^6$, which may be the same or different, each represents a hydrogen atom, an alkyl group having 1 to 5 carbon atoms, an alkoxy group having 1 to 5 carbon atoms, or a halogen atom; and $Z^\ominus$ represents an anion.

Another embodiment of this invention provides a photoconductive composition comprising a thiopyrylium compound represented by general formula (I)

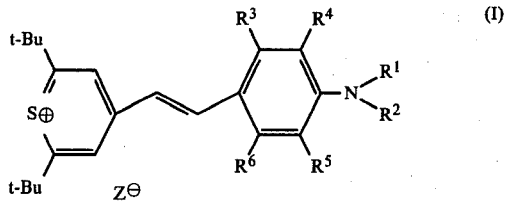

wherein t-Bu represents a tert-butyl group; $R^1$ and $R^2$, which may be the same or different, each represents a hydrogen atom, an alkyl group having 1 to 5 carbon atoms, a substituted alkyl group, an unsubstituted aryl group or a substituted aryl group, with the proviso that $R^1$ and $R^2$ are not simultaneously an alkyl group; $R^3$, $R^4$, $R^5$ and $R^6$, which may be the same or different, each represents a hydrogen atom, an alkyl group having 1 to 5 carbon atoms, an alkoxy group having 1 to 5 carbon atoms, or a halogen atom; and $Z^\ominus$ represents an anion.

DESCRIPTION OF PREFERRED EMBODIMENTS

Figure 1:
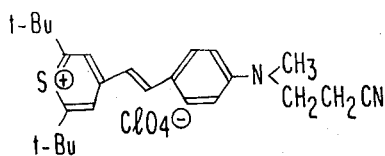
FIGS. 1 to 5 are absorption spectra of thiopyrylium compounds of this invention and compounds for comparison.
Figure 1:
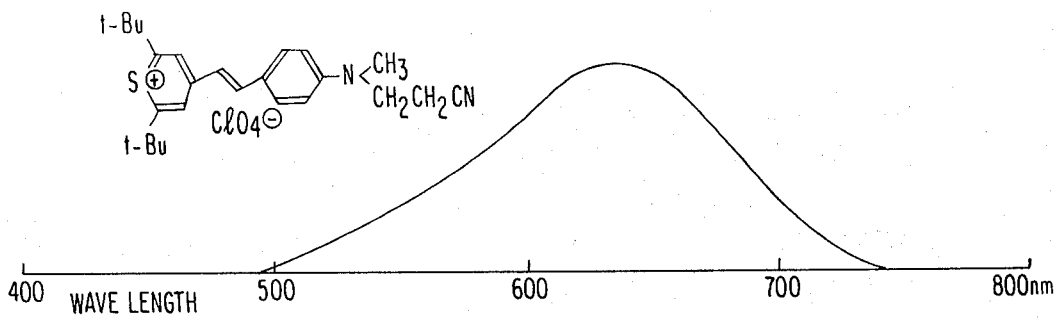

In general formula (I) shown above, alkyl groups having 1 to 5 carbon atoms and represented by $R^1$ and $R^2$ include a methyl group, an ethyl group, a propyl group, a butyl group, a pentyl group, an isopropyl group, an isobutyl group, an isoamyl group, a sec-butyl group, a neopentyl group, a tert-butyl group, a tert-pentyl group, etc.

Aryl groups represented by $R^1$ and $R^2$ include a phenyl group, an α-naphthyl group, a β-naphthyl group, etc.

In general formula (I) shown above, when $R^1$ and $R^2$ can be a substituted alkyl group, with examples of substituents being a cyano group, a halogen atom (e.g., a fluorine atom, a chlorine atom, a bromine atom, etc.), a hydroxy group, a carboxy group, an alkoxy group (having 1 to 5 carbon atoms and containing a straight or branched chain alkyl moiety) such as a methoxy group, an ethoxy group, an isopropoxy group, etc., an aryl group such as a phenyl group, a tolyl group, etc., an aryloxy group such as a phenoxy group, etc., an alkoxycarbonyl group (the alkyl moiety having 1 to 5 carbon atoms) such as a methoxycarbonyl group, an ethoxycarbonyl group, etc., or an acyloxy group (the acyl moiety being an alkylcarbonyl group having 1 to 5 carbon atoms, or a substituted or unsubstituted arylcarbonyl group) such as an acetoxy group, a benzoyloxy group, etc. $R^1$ and $R^2$ can also be a substituted aryl group, with examples of substituents being an alkyl group (a straight or branched chain alkyl group having 1 to 5 carbon atoms) such as a methyl group, an ethyl group, etc., an alkoxycarbonylalkyl group (the alkoxy moiety having 1 to 6 carbon atoms and the alkyl moiety having 1 to 6 carbon atoms) such as a (methoxycarbonyl)methyl group or an (ethoxycarbonyl)ethyl group, a (methoxycarbonyl)ethyl group, etc., an alkoxy group (having 1 to 5 carbon atoms and containing a straight or branched chain alkyl moiety) such as a methoxy group or an ethoxy group, etc., a halogen atom (e.g., a fluorine atom, a chlorine atom, a bromine atom, etc.), an amino group, such as a dialkylamino group having 1 to 8 carbon atoms, for example, a dimethylamino group, a diethylamino group, etc., a nitro group or a cyano group.

Specific examples of straight chain alkyl groups having 1 to 5 carbon atoms are a methyl group, an ethyl group, a propyl group, a butyl group, a pentyl group, etc., and specific examples of branched alkyl groups having 3 to 5 carbon atoms are an isopropyl group, an isobutyl group, an isoamyl group, a sec-butyl group, a neopentyl group, a tert-butyl group, a tert-pentyl group, etc. Examples of aryl groups are a phenyl group, an α-naphthyl group, a β-naphthyl group, etc.

Illustrative examples of preferred substituents for $R^1$ and $R^2$ are a methyl group, an ethyl group, a propyl group, a fluoromethyl group, a chloromethyl group, a 2-fluoroethyl group, a 2-chloroethyl group, a cyanomethyl group, a 2-cyanoethyl group, a hydroxymethyl group, a 2-hydroxyethyl group, a methoxymethyl group, a 2-methoxyethyl group, an ethoxymethyl group, a 2-ethoxyethyl group, a carboxymethyl group, a 2-carboxyethyl group, a methoxycarbonylmethyl group, a 2-(methoxycarbonyl)ethyl group, an ethoxycarbonylmethyl group, a 2-(ethoxycarbonyl)ethyl group, a phenoxymethyl group, a 2-phenoxyethyl group, a phenyl group, a p-tolyl group, an m-tolyl group, a p-ethylphenyl group, a p-methoxyphenyl group, a p-ethoxyphenyl group, a p-[2-(methoxycarbonyl)ethyl]phenyl group, a p-[2-(ethoxycarbonyl)ethyl]phenyl group, a p-(methoxycarbonylmethyl)phenyl group, a p-(ethoxycarbonylmethyl)phenyl group, etc. Also, $R^3$ to $R^6$ each can be, specifically, a hydrogen atom, a methyl group, an ethyl group, a methoxy group, an ethoxy group, a fluorine atom, a chlorine atom, etc.

Suitable anions shown by $Z^\ominus$ are known single atom ions having a negative charge and atomic group ions composed of a plurality of atoms, and an acid anion of an acid shown by HZ having a pKa below 5 is preferred, and further a strong acid anion having a pKa below 2 is more preferred. Specific examples of anions are a halogen anion such as fluoride ion, chloride ion, bromide ion, iodide ion, etc., for the single atom ion, and an organic anion such as trifluoroacetate ion, trichloroacetate ion, p-toluenesulfonate ion, etc., and an inorganic anion such as perchlorate ion, periodate ion, tetrachloroaluminate ion, trichloroferrate (II) ion, tetrafluoroborate ion, hexafluorophosphate ion, sulfate ion, hydrogensulfate ion, nitrate ion, etc., for the atomic group ions. Of these ions, where such is divalent anion, the anion is equivalent to two monovalent anions. Preferred examples of anions are chloride ion, bromide ion, perchlorate ion, tetrafluoroborate ion, p-toluenesulfonate ion, trifluoroacetate ion, etc.

The thiopyrylium compounds of this invention are novel compounds and have a main absorption near the red region, i.e., in the wavelength regions of 600 to 700 nm. However, since these thiopyrylium compounds have tert-butyl groups at the 2- and 6-positions of the thiopyrylium nucleus, they have substantially no side absorption near a wavelength of 400 nm, which appears in the case of known thiopyrylium compounds having conjugatable substituents at the 2- and 6-positions or a condensed ring of the conjugatable nucleus. Therefore, when the thiopyrylium compound of this invention is used as a sensitizing dye for an organic photoconductor which does not absorb visible light (i.e., is not sensitive to visible light), such as poly-N-vinylcarbazole, etc., a photosensitive material with beautiful color and without color mixing is obtained. Further, the photosensitive material containing the thiopyrylium compound of this invention does not cause yellow-mixed coloration so much even if it is exposed over a long time, because the thiopyrylium compound contained in the photosensitive material has no conjugated groups at the 2- and 6-positions which are seemed to be the cause of a discoloration, especially yellow-mixed coloration on a long-time exposure.

The photoconductive composition containing the thiopyrylium compound of this invention has higher sensitivity to red light than a photoconductive composition containing known thiopyrylium compounds having the same structure as the thiopyrylium compound of this invention except that the compound has conjugatable substituents, e.g., phenyl groups at the 2- and 6-positions and hence is particularly useful for an electrophotographic process using a light source in this region (e.g., a He-Ne laser with a wavelength of about 630 nm). Still further, the thiopyrylium compound of this invention can be effectively used for photoconductive photosensitive particles by incorporating the thiopyrylium compound into photoconductive photosensitive particles used in a photoelectrophoresis electrophotographic process.

The thiopyrylium compound of this invention can be prepared by the following process.

The compound of general formula (I) can be prepared by reacting 2,6-di-t-butyl-4-methylthiopyrylium salt shown by general formula (V) and a substituted benzaldehyde shown by general formula (VI). The compound (VI) is obtained by the procedures described in H. Eilingsfeld, Angewandte Chemie, 72, p. 836~ (1960).

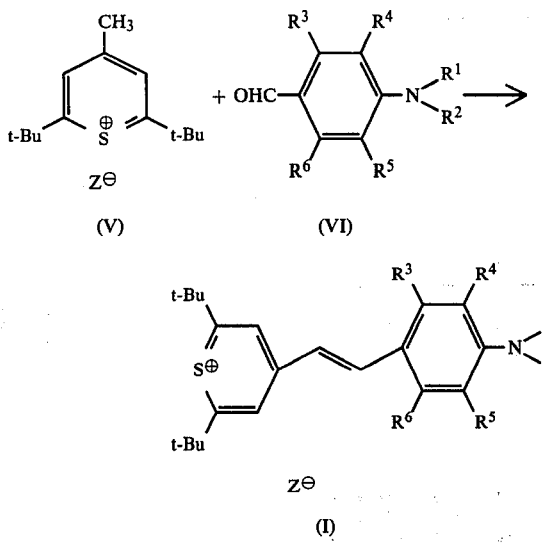

(V)   (VI)

(I)

wherein t-Bu represents a t-butyl group and $Z^\ominus$, $R^1$ to $R^6$ are the same as defined above.

The 2,6-di-t-butyl-4-methylthiopyrylium salt shown by formula (V) used as a starting material in this reaction is the compound newly synthesized by the inventors herein and synthesis processes are described in detail in the following patent applications by the inventors; i.e., Japanese Patent Application Nos. 81523/79, 81524/79, 81525/79 and 37249/79 and U.S. patent application Ser. No. 135,030, filed Mar. 28, 1980, now U.S. Pat. No. 4,343,948, the substance of which is incorporated herein by reference.

Thus, the thiopyrylium compounds of formula (I) prepared using these thiopyrylium salts are novel compounds. The compound of formula (I) can be synthesized in the following manner. First, 0.5–10 mol equivalent, preferably 1–2 mol equivalent, of the substituted benzaldehyde of formula (VI) is used per mol equivalent of the compound of formula (V).

The reaction of the compound of formula (V) and the compound of formula (VI) can be performed under one of the following three conditions.

(1) Performing the reaction by heating the reactants without using solvent or in a solvent.

In the case of using a solvent, various solvents may be used but an alcohol such as ethanol, etc., a nitrile such as acetonitrile, etc., a ketone such as methyl ethyl ketone, etc., a nitro compound such as nitrobenzene, etc., and a halogenated hydrocarbon such as tetrachloroethane, etc., are preferably used and further an alcohol such as ethanol, etc., is particularly preferred. The reaction temperature can be from about 50° C. to about 300° C. and the reaction time can be from 5 minutes to 3 hours, preferably from 10 minutes to 1 hour.

(2) Performing the reaction in the presence of an amine.

In this case, various solvents may be used but an alcohol such as ethanol, etc., a nitrile such as acetonitrile, etc., a ketone such as methyl ethyl ketone, etc., a nitro compound such as nitrobenzene, etc., and a halogenated hydrocarbon such as tetrachloroethane, etc., are preferably used and further an alcohol such as ethanol, etc., is particularly preferred.

Examples of amine used in this reaction are primary, secondary, and tertiary alkylamines having 1 to 25 carbon atoms, such as piperidine, triethylamine, hexylamine, etc.; aromatic amines having 6 to 25 carbon atoms, such as aniline, dimethylaniline, etc.; and nitrogen-containing unsaturated heterocyclic compounds such as pyridine, quinoline, etc.

The amount of the amine used is about 0.1 to 10 mols, preferably 0.5 to 2 mols, per mol of the thiopyrylium salt. Also, as the case may be, an excess amount of amine can be used as a solvent. The reaction time can range from about 30 minutes to 10 hours, preferably from 1 hour to 3 hours, and the reaction temperature can be from about 50° C. to the refluxing temperature of the amine, preferably at about the refluxing temperature of the amine. The amount of the solvent used is about 1 to 100 ml, preferably 3 to 10 ml, per gram of the compound of formula (V) used as the starting material.

(3) Performing the reaction in a carboxylic acid anhydride.

The amount of the carboxylic acid anhydride, such as, for example, acetic anhydride used is about 1 to 20 ml, preferably 2 to 10 ml, per gram of the starting material of formula (V). The reaction time is from about 1 minute to 3 hours, preferably 3 minutes to 10 hours. The reaction temperature is from about 80° C. to the refluxing temperature (about 140° C.), preferably about 100° C.

Examples of thiopyrylium compounds of this invention shown by formula (I) obtained by these processes include the compounds as shown in Table 1.

TABLE 1

| Thiopyrylium Compound | $R^1$ | $R^2$ | $R^3$ | $R^4$ | $R^5$ | $R^6$ | $Z^\ominus$ |
|---|---|---|---|---|---|---|---|
| 1 | —CH$_3$ | —CH$_2$CH$_2$CN | —H | —H | —H | —H | ClO$_4^\ominus$ |
| 2 | —CH$_2$CH$_2$Cl | —CH$_2$CH$_2$CN | —H | —H | —H | —H | ClO$_4^\ominus$ |
| 3 | —CH$_2$CH$_2$CN | —CH$_2$CH$_2$CN | —H | —H | —H | —H | BF$_4^\ominus$ |
| 4 | —CH$_2$CH$_2$Cl | —CH$_2$CH$_2$CN | —CH$_3$ | —H | —H | —H | BF$_4^\ominus$ |
| 5 | —CH$_2$CH$_2$OH | —CH$_2$CH$_2$OH | —H | —H | —H | —H | BF$_4^\ominus$ |
| 6 | —CH$_2$CH$_2$CN | —CH$_2$CH$_2$CN | —Cl | —H | —H | —H | BF$_4^\ominus$ |
| 7 | —CH$_2$—⟨Ph⟩ | —CH$_2$—⟨Ph⟩ | —CH$_3$ | —H | —H | —H | BF$_4^\ominus$ |

TABLE 1-continued

[Structure: thiopyrylium compound with t-Bu groups on S⊕ ring, connected via –CH=CH– to a phenyl ring bearing R³, R⁴, R⁵, R⁶ substituents and an N(R¹)(R²) group, with Z⊖ counterion]

| Thiopyrylium Compound | R¹ | R² | R³ | R⁴ | R⁵ | R⁶ | Z⊖ |
|---|---|---|---|---|---|---|---|
| 8 | $-CH_2-C_6H_4-NO_2$ | $-C_2H_5$ | $-H$ | $-H$ | $-H$ | $-H$ | $BF_4^{\ominus}$ |
| 9 | $-C_2H_4-O-C_6H_5$ | $-C_2H_4-O-C_6H_5$ | $-H$ | $-H$ | $-H$ | $-H$ | $BF_4^{\ominus}$ |
| 10 | $-C_2H_4OC_2H_5$ | $-C_2H_4OC_2H_5$ | $-H$ | $-H$ | $-H$ | $-H$ | $BF_4^{\ominus}$ |
| 11 | $-CH_3$ | $-CH_3$ | $-OCH_3$ | $-H$ | $-H$ | $-H$ | $BF_4^{\ominus}$ |
| 12 | $-C_2H_5$ | $-C_2H_4COOC_2H_5$ | $-H$ | $-H$ | $-H$ | $-H$ | $ClO_4^{\ominus}$ |
| 13 | $-C_2H_5$ | $-C_2H_4COOH$ | $-H$ | $-H$ | $-H$ | $-H$ | $BF_4^{\ominus}$ |
| 14 | $-CH_3$ | $-C_2H_4OCOCH_3$ | $-H$ | $-H$ | $-H$ | $-H$ | $BF_4^{\ominus}$ |
| 15 | $-C_6H_5$ | $-C_6H_5$ | $-H$ | $-H$ | $-H$ | $-H$ | $BF_4^{\ominus}$ |
| 16 | $-C_6H_4-CH_3$ | $-C_6H_4-CH_3$ | $-H$ | $-H$ | $-H$ | $-H$ | $BF_4^{\ominus}$ |
| 17 | $-C_6H_4-OCH_3$ | $-C_6H_4-OCH_3$ | $-H$ | $-H$ | $-H$ | $-H$ | $BF_4^{\ominus}$ |
| 18 | $-C_6H_5$ | $-C_6H_4-C_2H_4COOCH_3$ | $-H$ | $-H$ | $-H$ | $-H$ | $BF_4^{\ominus}$ |
| 19 | $-C_2H_5$ | $-C_2H_4OCOCH_3$ | $-H$ | $-H$ | $-H$ | $-H$ | $BF_4^{\ominus}$ |
| 20 | $-C_2H_4OCOCH_3$ | $-C_2H_4OCOCH_3$ | $-H$ | $-H$ | $-H$ | $-H$ | $BF_4^{\ominus}$ |
| 21 | $-C_2H_5$ | $-C_2H_4Cl$ | $-H$ | $-H$ | $-H$ | $-H$ | $ClO_4^{\ominus}$ |
| 22 | $-C_2H_4Cl$ | $-C_2H_4Cl$ | $-H$ | $-H$ | $-H$ | $-H$ | $ClO_4^{\ominus}$ |

The thiopyrylium compounds of this invention thus prepared can be used as sensitizers for inorganic or organic photoconductive materials for improving the photoconductivity and sensitivity characteristics of various photoconductive materials. Examples of inorganic photoconductive materials are zinc oxide, cadmium sulfide, etc., but particularly effective photoconductive materials are organic photoconductive materials.

When the thiopyrylium compounds of this invention are used as sensitizers for inorganic photoconductive materials, sometimes they do not show sufficient sensitizing action and this is considered to be due to the somewhat low adsorptive power of thiopyrylium compounds of this invention to inorganic photoconductive materials such as zinc oxide as compared with organic photoconductive materials, and the thiopyrylium compounds are desorbed from the inorganic photoconductive materials by the action of additional components such as binder, etc., present.

Therefore, in such a case, the electrophotograhic photosensitive material may be prepared by dispersing an inorganic photoconductive material in a binder composed of a resin which does not contain a polar group (e.g., a carboxy group, a hydroxy group, etc.) having a high affinity for the inorganic photoconductive material such as zinc oxide, thereby sensitization can be sufficiently attained. In using the thiopyrylium compound of this invention as a sensitizing dye for inorganic photoconductive material such as zinc oxide, etc., it is preferred to use a resin containing almost no polar groups, e.g., polystyrene, styrene-butadiene copolymer, etc., as a binder for the inorganic photoconductive material.

Examples of organic photoconductive materials which can be used in this invention are low molecular weight compounds and high molecular weight compounds. Low molecular weight photoconductive compounds include carbazoles such as carbazole, N-ethylcarbazole, etc.; triarylamines such as tri-p-tolylamine, triphenylamine, etc.; polyarylmethanes shown by

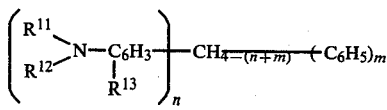

wherein $R^{11}$, $R^{12}$ and $R^{13}$ each is hydrogen; an alkyl group such as methyl, ethyl, propyl, etc.; or an aryl group such as phenyl or tolyl; condensed aromatic ring compounds such as anthracene, etc.; aromatic compounds containing an unsaturated bond, such as tetraphenylbutadiene, tetraphenylhexatriene, etc.; and unsaturated heterocyclic ring-containing compounds such as oxadiazole, thiadiazole, triazole, imidazole, pyrazoline, and various derivatives thereof.

Examples of high molecular weight compounds include poly-N-vinylcarbazole and derivatives thereof such as poly-N-vinylcarbazole, brominated poly-N-vinylcarbazole, etc.; polyvinylanthracene, polyacenaphthylene; polyvinylacridine; polyvinylphenothiazine; etc.

Preferred photoconductive materials include poly-N-vinylcarbazole; triarylamines such as tri-p-tolylamine, triphenylamine, etc.; polyarylamines such as 4,4'-bis(-diethylamino)-2,2'-dimethyltriphenylmethane, etc.; and unsaturated heterocyclic ring-containing compounds typified by pyrazoline derivatives such as 3-(4-dimethylaminophenyl)-1,5-diphenyl-2-pyrazoline, etc.

The photoconductive composition of this invention containing the thiopyrylium compound of this invention is obtained by dissolving the thiopyrylium compound (dye) and a photoconductive compound in an organic solvent. The photoconductive composition of this invention is used for a photosensitive material by coating the composition on an electrically conductive support in a conventional manner such as by blade coating, knife coating, reverse roll coating, dip coating, rod bar coating or spray coating followed by drying or is used for photoelectrophoresis as a dispersion prepared by forming particles of the composition from the organic solvent solution of the composition using a minispray apparatus and dispersing the particles in an electrically insulating liquid.

Suitable electrically conductive supports include aluminum-paper laminates; metal foils such as aluminum foil, zinc foil, etc.; metal plates such as aluminum plate, copper plate, zinc plate, brass plate, zinc-plated plate, etc.; and papers or films such as cellulose acetate films, polystyrene films, each vapor deposited with a metal such as chromium, silver, nickel, aluminum, etc.; and other papers rendered electrically conductive. Preferably, papers, cellulose acetate films, polyethylene terephthalate films with a vapor deposited layer of a metal such as chromium, silver, nickel, aluminum, etc., or a metal oxide such as indium oxide, etc., are used.

Volatile hydrocarbon solvents having boiling point of lower than 200° C. can be used as the organic solvent and, in particular, dichloromethane, chloroform, 1,2-dichloroethane, tetrachloroethane, dichloropropane or trichloroethane is preferably used. In addition to these materials, aromatic hydrocarbons such as chlorobenzene, toluene, xylene, and benzene; ketones such as acetone, 2-butanone, etc.; ethers such as tetrahydrofuran, etc.; methylene chloride; and other solvents which are usually used as solvents for coating compositions can be also used alone or as a mixture thereof. The amount of solvent used is about 1 to 100 g, preferably 5 to 20 g, per gram of the total amount of the thiopyrylium compound (dye), the photoconductive material, and other additives.

The amount of the thiopyrylium compound of this invention used as a sensitizer is about 0.0001 to 30 parts by weight, preferably 0.001 to 10 parts by weight, per 100 parts by weight of the photoconductive material used.

In one mode of using the photoconductive composition of this invention, the thipyrylium compound (sensitizer) is incorporated in particles used for a photoelectrophoretic process and images can be obtained in the photoelectrophoretic process. The particles used for the photoelectrophoretic process are prepared from a solution containing a photoconductive material such as poly-N-vinylcarbazole, the thiopyrylium compound sensitizer of this invention, and other additives using a minispraying means. These particles are used for a photoelectrophoretic process as a dispersion thereof in an electrically insulating liquid, for example, a saturated hydrocarbon such as decane, dodecane, octane, paraffin, isooctane, etc., preferably in a long chain alkyl hydrocarbon such as Isopar E, Isopar H, and Isopar G (trade names, made by Esso Chemical Co.). Isopar E, Isopar H, and Isopar G contain saturated hydrocarbons in an amount of 99.9% by weight, 99.3% by weight, and 99.8% by weight, respectively, and aromatic hydrocarbons in an amount of 0.05% by weight, 0.2% by weight, and 0.2% by weight, respectively. However, Isopar H contains less than 0.5% by weight olefin. The boiling points of these liquids are 115°–142° C., 174°–189° C., and 158°–177° C., respectively. The amount of the particles in the dispersion is about 0.5–10% by weight, preferably 1–3% by weight, of the dispersion. The photoelectrophoretic process and apparatus for the process are described in, for example, Japanese Patent Publication No. 20640/70 and U.S. Pat. No. 3,384,448.

The photoconductive layer and the particles described above may further contain appropriate additives for improving the properties of the photoconductive layer and the particles.

The photoconductive composition of this invention may contain an electrically insulating binder. A preferred binder for preparing the photoconductive composition of this invention is a film-forming hydro phobic polymer binder having a quite high dielectric breakdown strength and good electric-insulating property. Typical examples of such a polymer are vinyl resins; natural resins such as gelatin, cellulose ester derivatives, cellulose nitrate, etc.; polycondensates including polyesters and polycarbonates; silicone resins; alkyd resins including styrene-alkyd resin, etc.; paraffin; and various mineral waxes. Examples of specific polymers useful as the binder are described in the section "Electrophotographic Elements, Materials, and Processes", *Research Disclosure*, Vol. 109, pages 61-67.

In general, the amount of the binder present in the photoconductive composition of this invention can be varied over a wide range but typically the amount of the binder is in a range of from about 10% by weight to about 90% by weight based on the total amount of the photoconductive material and the binder.

In producing photoconductive particles, a charge controlling agent and a dispersion stabilizer may be added to the particles. In particular, a copolymer of lauryl methacrylate and styrene (copolymerization molar ratio of 4 to 2:1), a copolymer of 2-ethylhexyl methacrylate and styrene (copolymerization molar ratio of 4:2 to 1), or a copolymer of lauryl methacrylate and acrylic acid (copolymerization molar ratio of 9 to 6:1) having both charge controlling and dispersion stabilizing functions is advantageously used in this case.

Also, to improve the flexibility and strength, a plasticizer such as diphenyl chloride, dimethyl phthalate and an epoxy resin (Epicoat, trade name, produced by Shell International Chemicals Co.) may be incorporated in the photoconductive composition of this invention in an amount of up to about 60 parts by weight, preferably 10 to 40 parts by weight, per 100 parts by weight of the photoconductive composition.

The thickness of the photoconductive composition of this invention coated on an appropriate support can be widely varied. The thickness is usually, however, in the range of from about 1 $\mu$m to about 300 $\mu$m (before drying).

It has been found that the preferred thickness of the photoconductive composition of this invention before drying is in the range of from about 2 $\mu$m to about 150 $\mu$m. However, useful results are also obtained even outside this range. The dry thickness of the coated photoconductive composition may be in a range of from about 1 $\mu$m to about 50 $\mu$m.

The photoconductive composition of this invention can be also used as a photoconductive layer for image pickup tubes of a video camera and as a photoconductive layer for a solid image pickup element with a light-receiving layer (photoconductive layer) formed over the entire surface of a semiconductor circuit one-dimensionally or two-dimensionally arranged for performing the transmission or scanning of signals.

The invention is further described more specifically by the following examples. Unless otherwise indicated, all parts, percents, ratios and the like are by weight.

EXAMPLE 1

2,6-Di-t-butyl-4-[4-(N-methyl-N-2-cyanoethylamino)-styryl]thiopyrylium perchlorate [Compound (1)]

In 1 ml of acetic anhydride were heated 65 mg of 2,6-di-t-butyl-4-methylthiopyrylium perchlorate (Compound (V)) and 40 mg of 4-(N-methyl-N-2-cyanoethylamino)benzaldehyde (Compound (VI)) for 30 minutes to 140° C. The reaction mixture was allowed to cool and diethyl ether was added to the reaction mixture to form crystals, which were recovered by filtration and recrystallized from ethyl acetate. The amount of the product obtained was 20 mg and the melting point was 176° C.

From elemental analysis and the spectral analysis, the product was confirmed to be 2,6-di-t-butyl-4-[4-(N-methyl-N-2-cyanoethylamino)styryl]thiopyrylium perchlorate (Compound (1)).

| Elemental Analysis for $C_{25}H_{33}ClO_4N_2S$: | | | |
|---|---|---|---|
| | C | H | N |
| Calculated (%): | 60.90 | 6.73 | 5.68 |
| Found (%): | 61.03 | 6.80 | 5.53 |

Infrared Absorption Spectra (cm$^{-1}$): 1552, 1525, 1175, and 1090

Ultraviolet and Visible Absorption Spectra: nm (log $\epsilon$), in acetonitrile: 584 nm (4.77) and 310 nm (4.07)

EXAMPLE 2

2,6-Di-t-butyl-4-[4-(N-2-cyanoethyl-N-2-chloroethylamino)styryl]thiopyrylium perchlorate [Compound (2)]

In 1 ml of acetic anhydride were heated 60 mg of 2,6-di-t-butyl-4-methylthiopyrylium perchlorate (Compound (V)) and 45 mg of 4-(N-2-cyanoethyl-N-2-chloroethylamino)benzaldehyde (Compound (VI)) for 40 minutes to 140° C. The reaction mixture was allowed to cool and diethyl ether was added to the reaction mixture to form crystals, which were recovered by filtration and recrystallized from ethyl acetate. The amount of the product was 30 mg and the melting point was 188° C.

From elemental analysis and spectral analysis, the product was confirmed to be 2,6-di-t-butyl-4-[4-(N-2-cyanoethyl-N-2-chloroethylamino)styryl]thiopyrylium perchlorate (Compound (2)).

| Elemental Analysis for $C_{26}H_{34}Cl_2O_4N_2S$: | | | |
|---|---|---|---|
| | C | H | N |
| Calculated (%): | 57.67 | 6.33 | 5.17 |
| Found (%): | 57.47 | 6.41 | 5.31 |

Infrared Absorption Spectra (cm$^{-1}$): 1562, 1550, 1520, 1182, 1120, and 1095

Ultraviolet and Visible Absorption Spectra: nm (log $\epsilon$), in acetonitrile: 564 nm (4.76) and 308 nm (4.12)

EXAMPLE 3

2,6-Di-t-butyl-4-[4-(diphenylamino)styryl]thiopyrylium tetrafluoroborate [Compound (15)]

In 1 ml of acetic anhydride were heated 62 mg of 2,6-di-t-butyl-4-methylthiopyrylium tetrafluoroborate (Compound (V)) and 55 mg of 4-(diphenylamino)benzaldehyde (Compound (VI)) for 40 minutes to 140° C. The reaction mixture was allowed to cool and diethyl ether was added to the reaction mixture to form crystals, which were recovered by filtration and recrystallized from ethyl acetate. The amount of the product was 45 mg and the melting point was 255°–256° C.

From elemental analysis and spectral analysis, the product was confirmed to be 2,6-di-t-butyl-4-[4-(diphenylamino)styryl]thiopyryllium tetrafluoroborate (Compound (15)).

| Elemental Analysis for $C_{33}H_{36}NBF_4S$: | | | |
|---|---|---|---|
| | C | H | N |
| Calculated (%): | 70.09 | 6.42 | 2.47 |
| Found (%): | 69.87 | 6.45 | 2.31 |

Infrared Absorption Spectra (cm$^{-1}$): 1568, 1550, 1495, 1178, and 1082

Ultraviolet and Visible Absorption Spectrum nm (log $\epsilon$), in acetonitrile: 580 nm (4.56) and 308 nm (4.27)

EXAMPLE 4

In 15 ml of 1,2-dichloroethane were dissolved 1 g of poly-N-vinylcarbazole and 2.55 mg of Thiopyrylium Compound (1) and the solution was coated on a polyethylene terephthalate film of 100 $\mu$m thick having a vapor deposited layer of indium oxide thereon using a rod bar followed by drying for 2 hours at 55° C. to produce a photosensitive material having a photoconductive layer. The thickness of the photoconductive layer was 2.0 μm. The absorption spectrum of the photoconductive material was as shown in FIG. 1 of the accompanying drawing. That is, the maximum absorption wavelength was 634 nm and the photosensitive material had no side absorption near 400 nm and showed a beautiful green appearance without color mixing.

After charging the photosensitive material to +320 volts using a commercially available corona device of +6 kilovolts, the photosensitive material was exposed to monochromatic light of 634 nm and the exposure amount until the surface potential reached ½ of the initial surface potential (the half decay exposure amount is denoted by $E_{\frac{1}{2}}$) was 80 ergs/cm². Also, the half decay exposure amount for the photosensitive material similarly exposed to monochromatic light of 630 nm was 93 ergs/cm².

Also, xerographic gain (the quality of electricity generated per photon absorbed, which shows the sensitization effect, details of which gain are described in P. J. Regensburger, *Photochemistry and Photobiology*, Vol. 8, pages 429-440 (1968)) was 0.30.

EXAMPLES 5 AND 6

In Example 5 Photosensitive Material A was prepared using 2.81 mg of Thiopyrylium Compound (2) in the same manner as in Example 4. Also, in Example 6 Photosensitive Material B was prepared using 2.93 mg of Thiopyrylium Compound (15) in the same manner as in Example 4.

Figure 2:
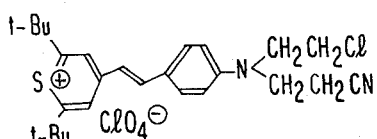
Figure 2:
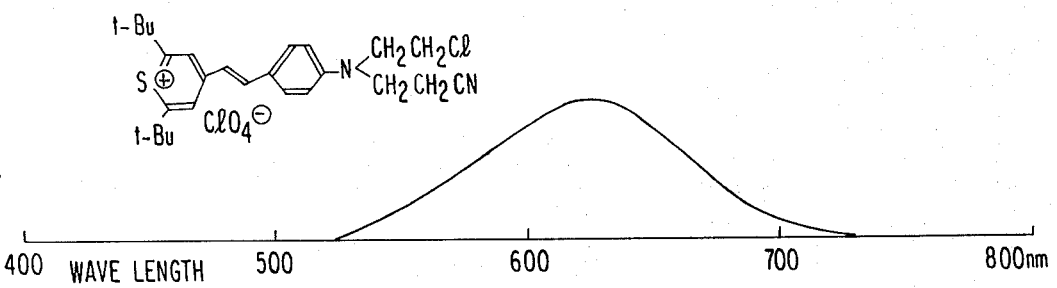
Figure 3:
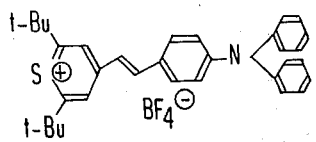
Figure 3:
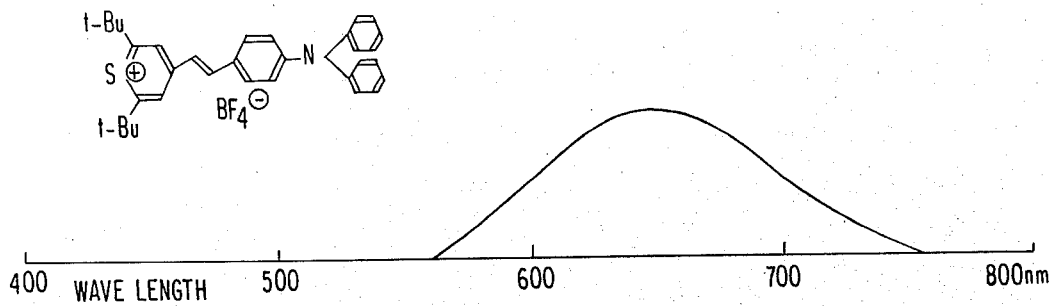

The absorption spectra of these photosensitive materials are shown in FIG. 2 and FIG. 3, respectively.

Also, the maximum absorption (λ max), the half decay exposure amount on irradiation with light of λ max ($E_{\frac{1}{2}}$ (λ max)), the xerographic gain of this invention (GAIN), and the half decay exposure amount on irradiation with light of 630 nm ($E_{\frac{1}{2}}$ (630 nm)) for each of these photosensitive materials are shown in Table 2 below.

TABLE 2

| Photosensitive Material | λmax (nm) | $E_{\frac{1}{2}}$ (λmax) (erg/cm²) | GAIN | $E_{\frac{1}{2}}$ (630 nm) (erg/cm²) |
| --- | --- | --- | --- | --- |
| A | 620 | 158 | 0.25 | 173 |
| B | 646 | 130 | 0.29 | 158 |

COMPARISON EXAMPLES 1 AND 2

In Comparison Example 1, Photosensitive Material C was prepared using 2.66 mg of Compound (VII) shown below

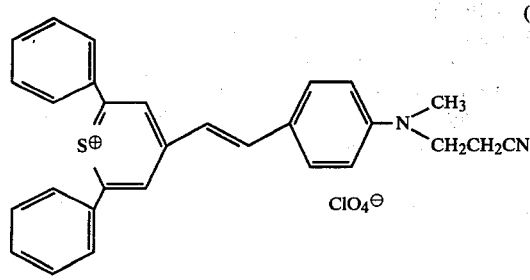

(VII)

in the same manner as in Example 4 and in Comparison Example 2, Photosensitive Material D was prepared using 2.95 mg of Compound (VIII) shown below

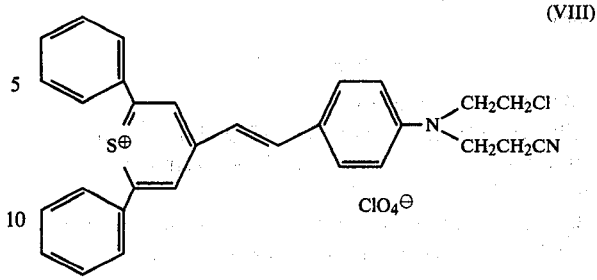

(VIII)

in the same manner as above.

Figure 4:
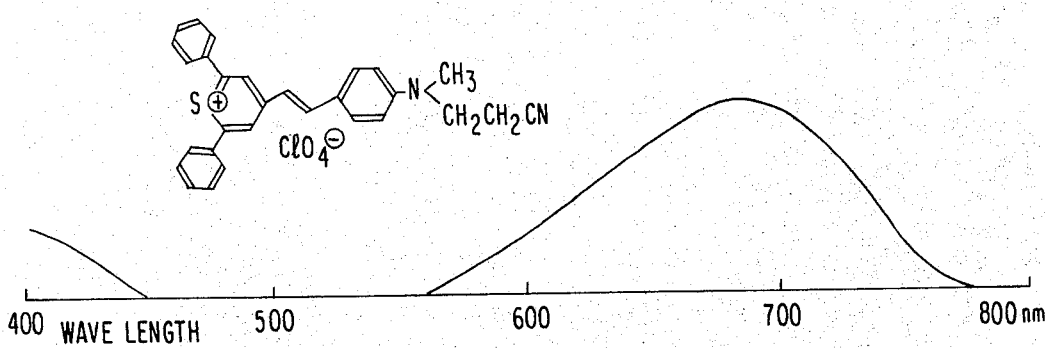
Figure 5:
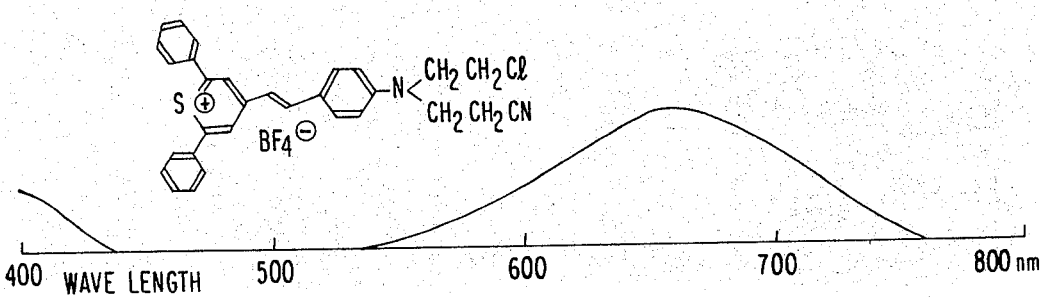

The absorption spectra of these photosensitive materials are shown in FIG. 4 and FIG. 5, respectively. Each of the photosensitive materials exhibited a muddy color due to side absorption near the wavelength of 400 nm as compared with the photosensitive materials in Examples 4 and 5.

Also, the sensitivities of these photosensitive materials measured in the same manner as in Example 5 and 6 are shown in Table 3 below.

TABLE 3

| Photosensitive Material | λmax (nm) | $E_{\frac{1}{2}}$ (λmax) (erg/cm²) | GAIN | $E_{\frac{1}{2}}$ (630 nm) (erg/cm²) |
| --- | --- | --- | --- | --- |
| C | 684 | 110 | 0.21 | 230 |
| D | 662 | 195 | 0.22 | 283 |

By comparing the results in Examples 4 and 5 with the results in Comparison Examples 1 and 2, it is clear that the photoconductive compositions using the thiopyrylium compounds of this invention having tertbutyl groups at the 2- and 6-positions thereof showed increased sensitivities at λ max and at a wavelength of 630 nm as compared with the photoconductive compositions using thiopyrylium compounds having similar structures to those of the thiopyrylium compounds of this invention but with phenyl groups at the 2- and 6-positions.

EXAMPLE 7

In order to examine a yellow-mixed coloration of photosensitive materials caused by an exposure to sunlight, the following experiments were made.

The photosensitive materials obtained in Example 5 and in Comparison Example 1 are exposed to sunlight through window-pane facing the south for 5 days. Absorbances at 400 nm of wavelength before and after exposure are shown below.

TABLE 4

| Photosensitive Material | Before Exposure | After Exposure |
| --- | --- | --- |
| A | 0.00 | 0.08 |
| D | 0.04 | 0.15 |

It is apparent from the results above described that the photosensitive material containing the dye of the present invention having substituents of t-butyl groups at 2- and 6-positions of thiopyrylium nucleus is superior to that having substituents of phenyl groups at 2- and 6-positions in a degree of yellow-mixed coloration.

EXAMPLE 8

Compounds 19 to 22 were prepared in the same manner as in Examples 1 to 3.

The compounds showed the following physical properties.

Compound 19

Melting Point: 175° to 176° C.
Elemental Analysis (%): C 61.48, H 6.86, N 2.67
Infrared Absorption Spectra (Wave Numbers cm$^{-1}$)
2960, 1740, 1550, 1520 and 1172
Ultraviolet and Visible Absorption Spectra (in acetonitrile): Maximum Wavelength 604 nm, log $\epsilon$ 4.75

Compound 20

Melting Point: 152° C.
Elemental Analysis (%): C 59.78, H 6.87, N 2.35
Infrared Absorption Spectra (Wave Numbers cm$^{-1}$)
2970, 1735, 1552, 1518 and 1180
Ultraviolet and Visible Absorption Spectra (in acetonitrile): Maximum Wavelength 588 nm, log $\epsilon$ 4.82

Compound 21

Melting point: 187° to 189° C.
Elemental Analysis (%): C 58.1, H 6.40, N 2.69
Infrared Absorption Spectra (Wave Numbers cm$^{-1}$)
2960, 1550, 1515 and 1160
Ultraviolet and Visible Absorption Spectra (in acetonitrile): Maximum Wavelength 596 nm, log $\epsilon$ 4.82

Compound 22

Melting Point: 202° to 203° C.
Elemental Analysis (%): C 54.60, H 5.77, N 2.31
Infrared Absorption Spectra (Wave Numbers cm$^{-1}$)
2970, 1552, 1537 and 1170
Ultraviolet and Visible Absoption Spectra (in acetonitrile): Maximum Wavelength 570 nm, log $\epsilon$ 4.79

EXAMPLE 9

Photosensitive Materials (1) to (22) were prepared using $5.18 \times 10^{-6}$ mol of each of Thiopyrylium Compounds (1) to (22) shown in Table 1 in the same manner as in Example 4.

After charging each of the photosensitive material to +250 volts using a commercially available corona device of +6 kilovolts, each photosensitive material was exposed to a halogen lamp and the exposure amount until the surface potential became ½ of the original surface potential ($E_{½}$) (lux.sec) was measured. The results are shown in Table 5 below.

TABLE 5

| Photosensitive Material | $E_{½}$ (lux-sec) |
|---|---|
| (1) | 32 |
| (2) | 28 |
| (3) | 35 |
| (4) | 43 |
| (5) | 25 |
| (6) | 23 |
| (7) | 31 |
| (8) | 42 |
| (9) | 20 |
| (10) | 26 |
| (11) | 27 |
| (12) | 31 |
| (13) | 33 |
| (14) | 29 |
| (15) | 21 |
| (16) | 42 |
| (17) | 37 |
| (18) | 29 |
| (19) | 30 |
| (20) | 27 |
| (21) | 25 |
| (22) | 29 |

While the invention has been described in detail and with reference to specific embodiments thereof, it will be apparent to one skilled in the art that various changes and modifications can be made therein without departing from the spirit and scope thereof.

What is claimed is:

1. A thiopyrylium compound of the general formula (I)

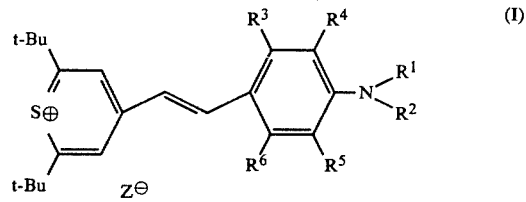

wherein t-Bu represents a tertiary butyl group; $R^1$ and $R^2$, which may be the same or different, each represents a hydrogen atom, an alkyl group having 1 to 5 carbon atoms, a substituted alkyl group wherein the substituent of the substituted alkyl group is a cyano group, a halogen atom, a hydroxy group, a carboxy group, an alkoxy group having 1 to 5 carbon atoms, an aryl group, an aryloxy group, an alkoxycarbonyl group having an alkyl moiety of 1 to 5 carbon atoms, or an acyloxy group, an unsubstituted aryl group, or a substituted aryl group wherein the substituent of the substituted aryl group is an alkyl group having 1 to 5 carbon atoms, an alkoxycarbonylalkyl group having an alkoxy moiety of 1 to 6 carbon atoms and an alkyl moiety of 1 to 6 carbon atoms, an alkoxy group having 1 to 5 carbon atoms, a halogen atom, an amino group, a nitro group or a cyano group, with the proviso that both $R^1$ and $R^2$ are not both an alkyl group; $R^3$, $R^4$, $R^5$ and $R^6$, which may be the same or different, each represents a hydrogen atom, an alkyl group having 1 to 5 carbon atoms, an alkoxy group having 1 to 5 carbon atoms, or a halogen atom; and $Z^-$ represents an anion.

* * * * *